US012596161B2

(12) United States Patent
Moulton et al.

(10) Patent No.: US 12,596,161 B2
(45) Date of Patent: Apr. 7, 2026

(54) METHODS AND SYSTEMS FOR ADJUSTING SUBJECT TABLE BEHAVIORS

(71) Applicant: GE Precision Healthcare LLC, Waukesha, WI (US)

(72) Inventors: Andrew Moulton, Waukesha, WI (US); Mark David Schmieding, Pewaukee, WI (US); Julie Silvers, Milwaukee, WI (US); Nicolas Escobar, Milwaukee, WI (US); Jiaqi Li, Pewaukee, WI (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 346 days.

(21) Appl. No.: 18/449,595

(22) Filed: Aug. 14, 2023

(65) Prior Publication Data
US 2025/0060433 A1 Feb. 20, 2025

(51) Int. Cl.
G01R 33/30 (2006.01)
A61B 5/00 (2006.01)
G01R 33/54 (2006.01)

(52) U.S. Cl.
CPC ............ G01R 33/307 (2013.01); A61B 5/704 (2013.01); G01R 33/546 (2013.01)

(58) Field of Classification Search
CPC ........... A61B 5/00; A61B 5/055; A61B 5/704; A61B 2562/0223; G01R 33/30; G01R 33/54; G01R 33/288; G01R 33/307; G01R 33/546
See application file for complete search history.

(56) References Cited

U.S. PATENT DOCUMENTS

| | | | |
|---|---|---|---|
| 11,226,632 B2 | 1/2022 | Biber | |
| 2014/0237721 A1* | 8/2014 | Lemire ................ | A61G 7/1046 |
| | | | 188/1.12 |
| 2016/0089283 A1* | 3/2016 | DeLuca ................... | A61G 7/08 |
| | | | 180/413 |
| 2017/0248665 A1* | 8/2017 | Ludwig ............. | G01R 33/3415 |
| 2018/0231622 A1* | 8/2018 | Hetz ...................... | A61B 5/055 |
| 2018/0329422 A1* | 11/2018 | Biber ................... | G05D 1/0088 |
| 2022/0047218 A1* | 2/2022 | Neuber ................. | A61B 5/704 |
| 2023/0072582 A1 | 3/2023 | Nufer et al. | |

FOREIGN PATENT DOCUMENTS

| | | | | |
|---|---|---|---|---|
| JP | H11151306 A | * | 6/1999 | ............. A61B 5/055 |

OTHER PUBLICATIONS

Espacenet English translation JP H11151306 A (Year: 1999).*

* cited by examiner

*Primary Examiner* — Eman A Alkafawi
*Assistant Examiner* — Courtney G Mcdonnough
(74) *Attorney, Agent, or Firm* — McCoy Russell LLP

(57) ABSTRACT
Various methods and systems are provided for adjusting behavior of a manually driven subject table based on a strength and/or a direction of a magnetic field as detected by a passive sensor of the manually driven subject table. In some embodiments, a medical imaging system comprises a manually driven subject table having a passive sensor configured to detect in real-time a strength or a direction of a magnetic field, and a controller communicably coupled to the passive sensor and configured with instructions stored on non-transitory memory that, when executed, cause the controller to augment transmission of a user input to one or more actuators of the manually driven subject table based on the strength or the direction of the magnetic field as detected by the passive sensor.

18 Claims, 10 Drawing Sheets

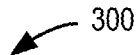

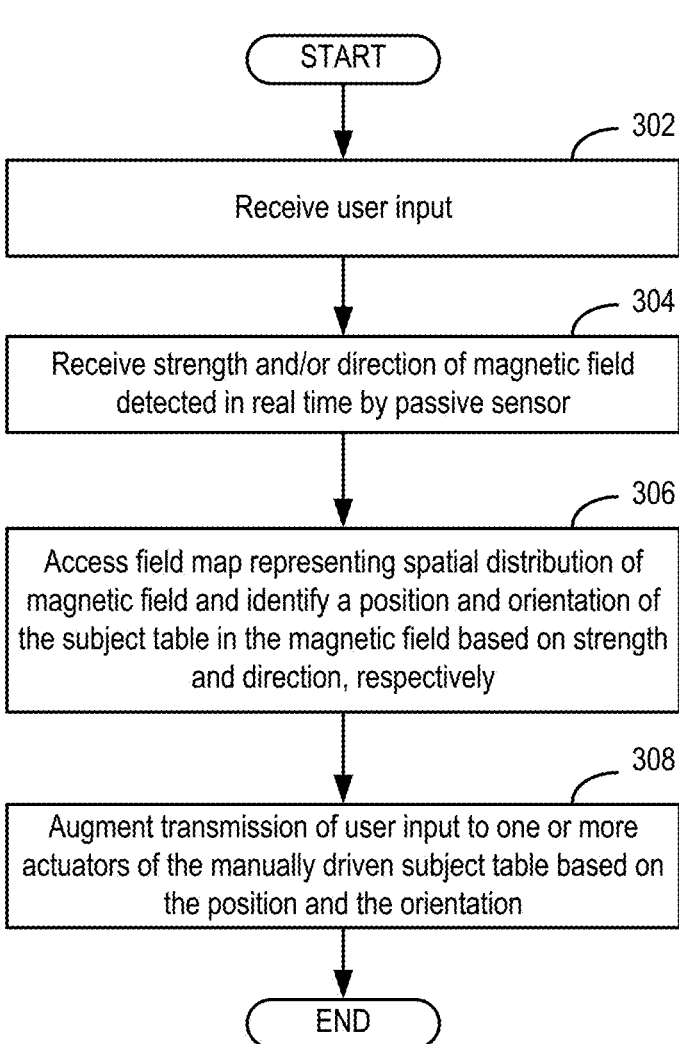

START

302

Receive user input

304

Receive strength and/or direction of magnetic field detected in real time by passive sensor

306

Access field map representing spatial distribution of magnetic field and identify a position and orientation of the subject table in the magnetic field based on strength and direction, respectively

308

Augment transmission of user input to one or more actuators of the manually driven subject table based on the position and the orientation

END

FIG. 3

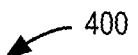

400

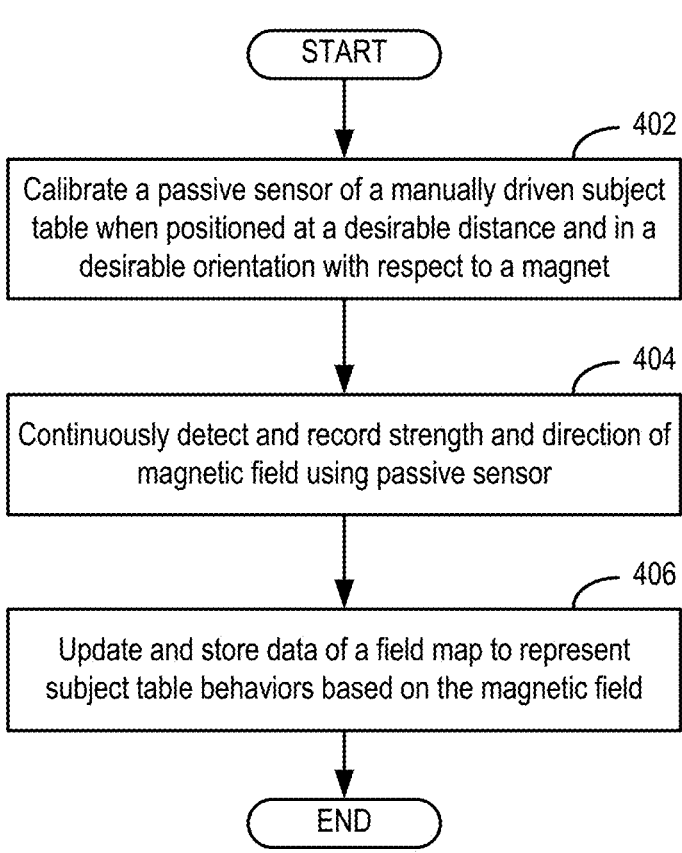

START

402

Calibrate a passive sensor of a manually driven subject table when positioned at a desirable distance and in a desirable orientation with respect to a magnet

404

Continuously detect and record strength and direction of magnetic field using passive sensor

406

Update and store data of a field map to represent subject table behaviors based on the magnetic field

END

FIG. 4

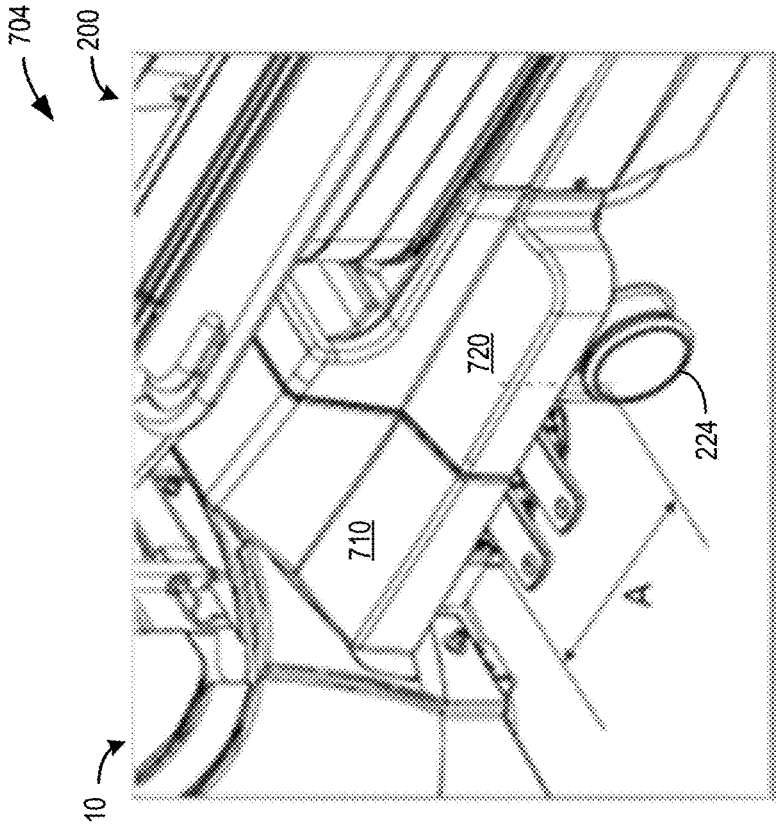
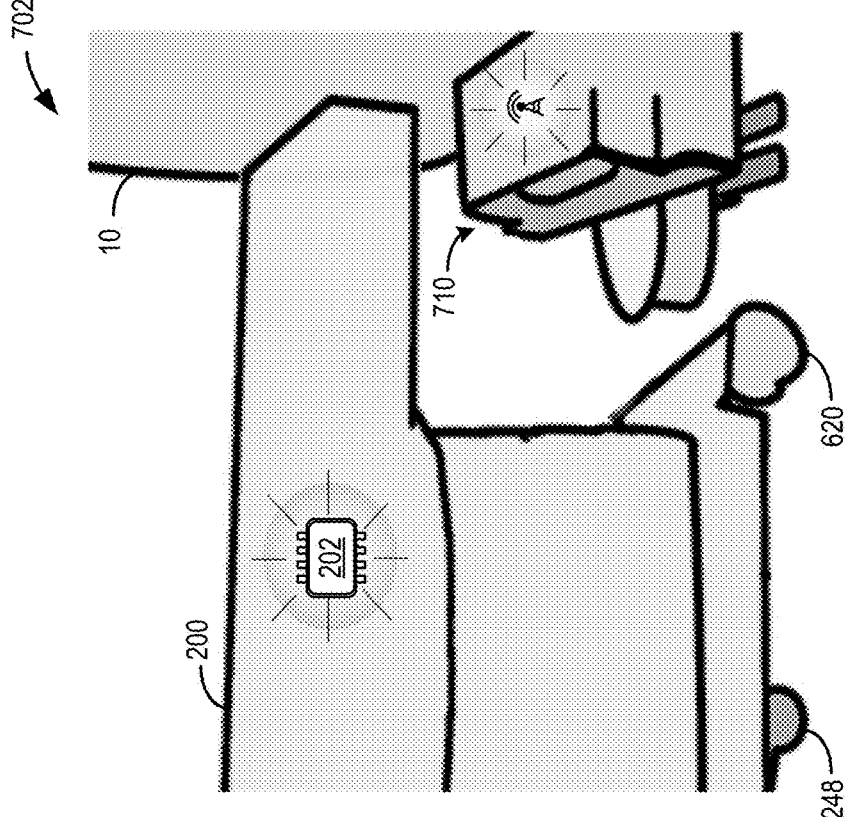
FIG. 7

METHODS AND SYSTEMS FOR ADJUSTING SUBJECT TABLE BEHAVIORS

FIELD

Embodiments of the subject matter disclosed herein relate to magnetic resonance imaging, and more particularly, to adjusting behavior of a manually driven subject table in response to a strength and a direction of a magnetic field of a magnetic system.

BACKGROUND

Magnetic resonance imaging (MRI) is a medical imaging modality that can create images of the inside of a human body without using x-rays or other ionizing radiation. MRI systems include a superconducting magnet to create a strong, uniform, static magnetic field $B_0$. When a human body, or part of a human body, is placed in the magnetic field $B_0$, the nuclear spins associated with the hydrogen nuclei in tissue water become polarized, wherein the magnetic moments associated with these spins become preferentially aligned along the direction of the magnetic field $B_0$, resulting in a small net tissue magnetization along that axis. MRI systems also include gradient coils that produce smaller amplitude, spatially-varying magnetic fields with orthogonal axes to spatially encode the magnetic resonance (MR) signal by creating a signature resonance frequency at each location in the body. The hydrogen nuclei are excited by a radio frequency signal at or near the resonance frequency of the hydrogen nuclei, which add energy to the nuclear spin system. As the nuclear spins relax back to their rest energy state, they release the absorbed energy in the form of an RF signal. This RF signal (or MR signal) is detected by one or more RF coils and is transformed into the image using reconstruction algorithms. Outside of the MRI system (e.g., within a room in which the MRI system is positioned), a magnitude and a direction of the magnetic field is based on a position within the room.

BRIEF DESCRIPTION

In one embodiment, a medical imaging system comprises a manually driven subject table having a passive sensor configured to detect in real-time a strength or a direction of a magnetic field, and a controller communicably coupled to the passive sensor and configured with instructions stored on non-transitory memory that, when executed, cause the controller to augment transmission of a user input to one or more actuators of the manually driven subject table based on the strength or the direction of the magnetic field as detected by the passive sensor.

A method for controlling a manually driven subject table comprises receiving a user input to the manually driven subject table, receiving a strength and a direction of a magnetic field detected in real-time using a passive sensor implemented in a manually driven subject table, accessing a field map representing a spatial distribution of the magnetic field and identifying a position and an orientation of the manually driven subject table based on the strength and the direction, respectively, of the magnetic field, and augmenting transmission of the user input to one or more actuators of the manually driven subject table based on the position and the orientation of the manually driven subject table.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIG. 3 illustrates a method for augmenting transmission of a user input to one or more actuators of the manually driven subject table of FIG. 2 based on a strength or a direction of a magnetic field as detected by the passive sensor, according to an embodiment of the disclosure.

FIG. 4 illustrates a method for calibrating one or more passive sensors of the subject table of FIG. 2, according to an embodiment of the disclosure.

FIG. 7 is an illustration of augmenting transmission of a user input to one or more docking system actuators of the manually driven subject table of FIG. 2 based on a strength or a direction of a magnetic field as detected by the passive sensor, according to an embodiment of the disclosure.

DETAILED DESCRIPTION

The following description relates to various embodiments for systems and methods for a manually driven subject table having a passive sensor configured to detect in real-time a strength or a direction of a magnetic field. The passive sensor may be any sensor which detects and responds to energy available in an environment without itself outputting energy to elicit a response from the environment. The passive sensor described herein is configured to detect at least one of a strength of a magnetic field or a direction of a magnetic field in real-time. For example, the passive sensor may be a Hall sensor. The manually driven subject table further includes one or more actuators which are communicably coupled to a controller. The one or more actuators of the manually driven subject table may augment user input behaviors of the manually driven subject table. For example, the controller may add, remove, or augment a maximum speed threshold of the manually driven subject table based on a position and an orientation of the manually driven subject table as detected by the passive sensor. In response to a user input having a force which causes a speed of the manually driven subject table to equal or exceed the maximum speed threshold, the controller may augment the user input by actuating a brake of one or more undriven wheels or of a drive wheel to reduce the speed of the manually driven subject table. In another example, the controller may direct user input based on a position and an orientation of the manually driven subject table as detected by the passive sensor. For example, the manually driven subject table may include a height actuator which may enable adjustment of a height of the manually driven subject table via an adjustable height mechanism. In response to the manually driven subject table being at an undesirable height as detected by the passive sensor based on the detected magnetic field, the controller may output a notification to a display device indicating a desired height adjustment. Additional actuators and respective augmentations to user input behaviors of the manually driven subject table are described herein. In this way, user-input behaviors of the manually driven subject table may be augmented based on a position, including proximity and orientation, of the manually driven subject table with respect to a source of a magnetic field. This may assist in positioning the manually driven subject table in a desired position with respect to the source of the magnetic field.

Figure 1:
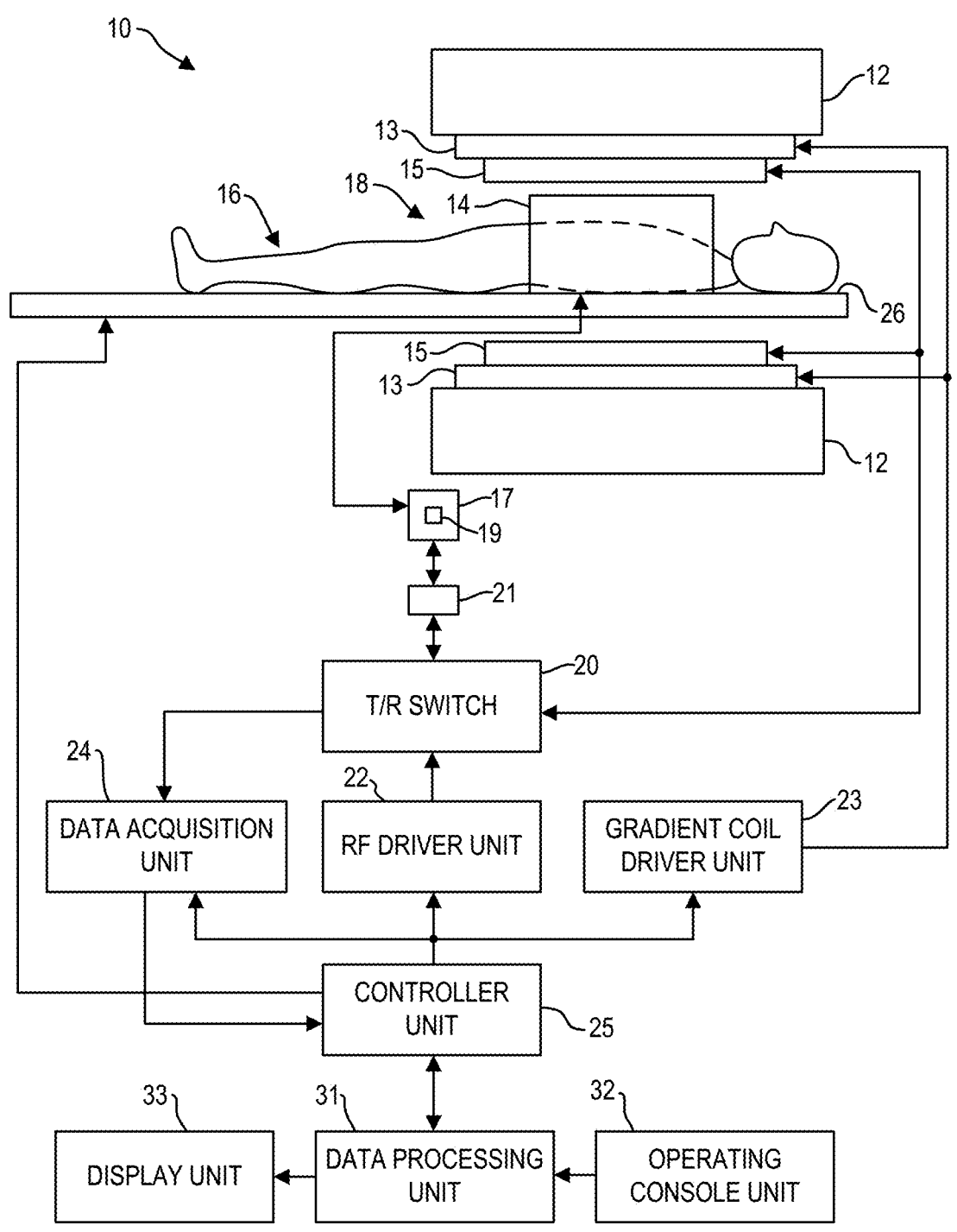
FIG. 1 is a block diagram of an MRI system, according to an embodiment of the disclosure.
Figure 2:
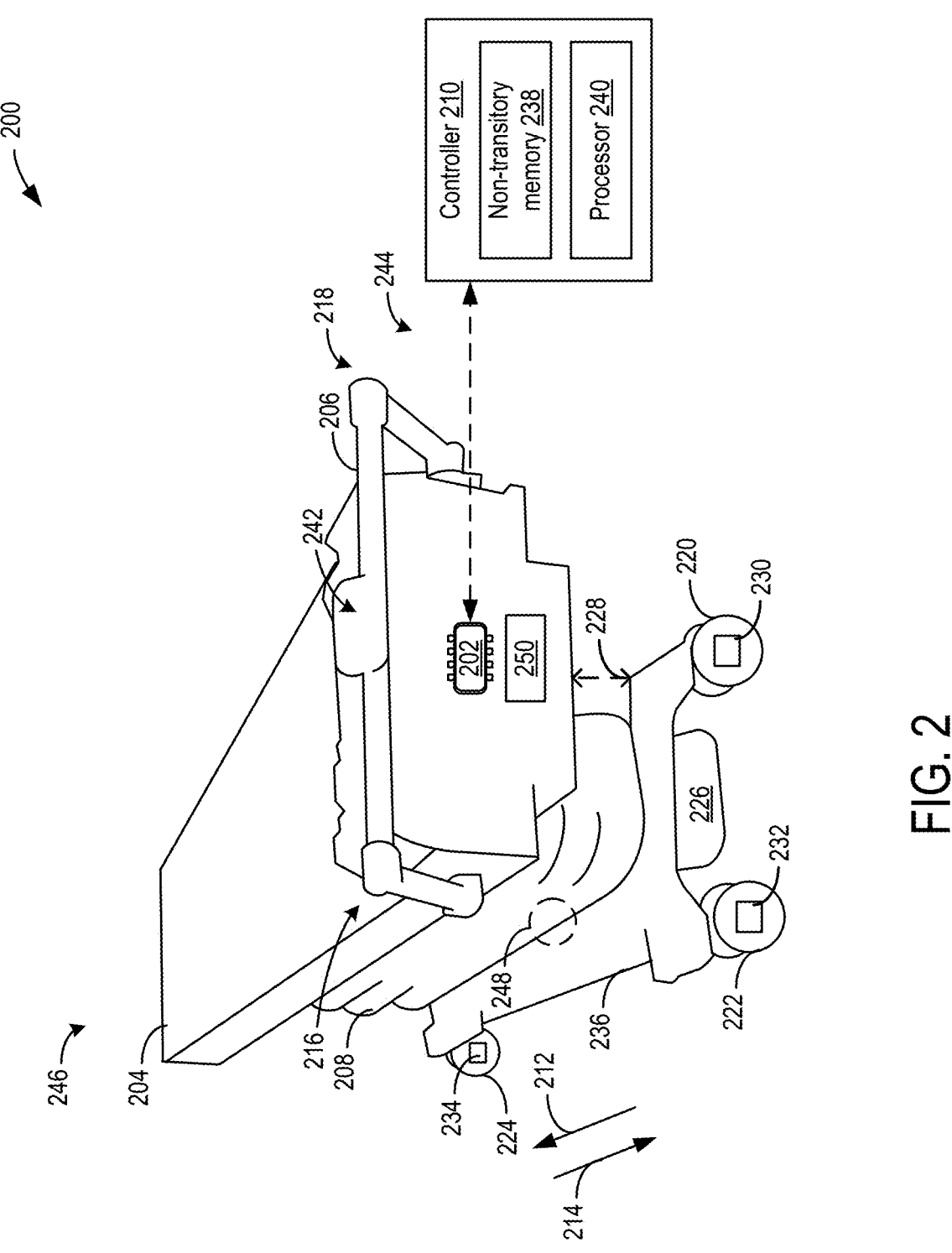
FIG. 2 is a manually driven subject table, including a passive sensor, according to an embodiment of the disclosure.
Figure 5:
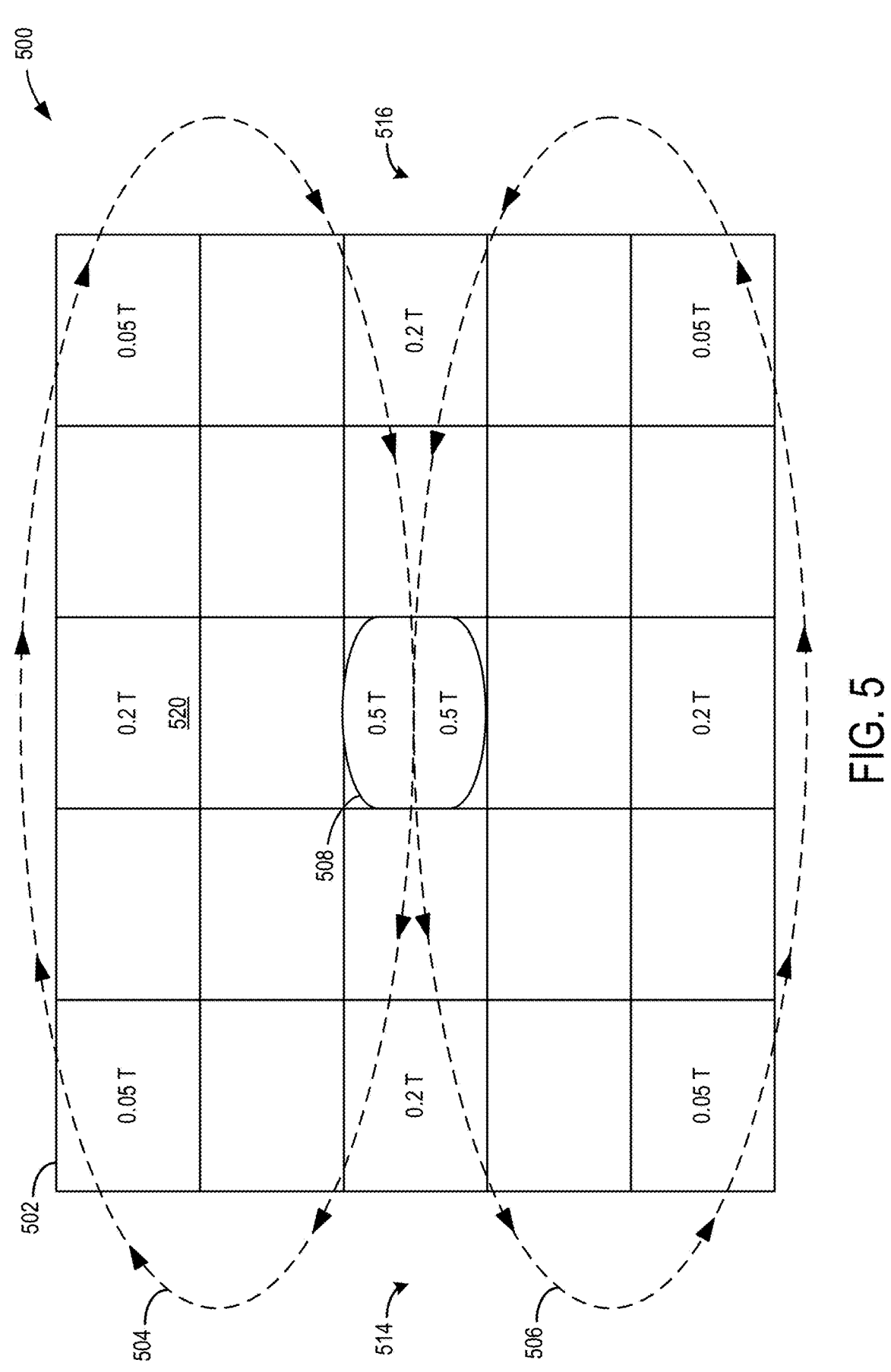
FIG. 5 illustrates an example field map of a magnetic field, according to an embodiment of the disclosure.
Figure 6:
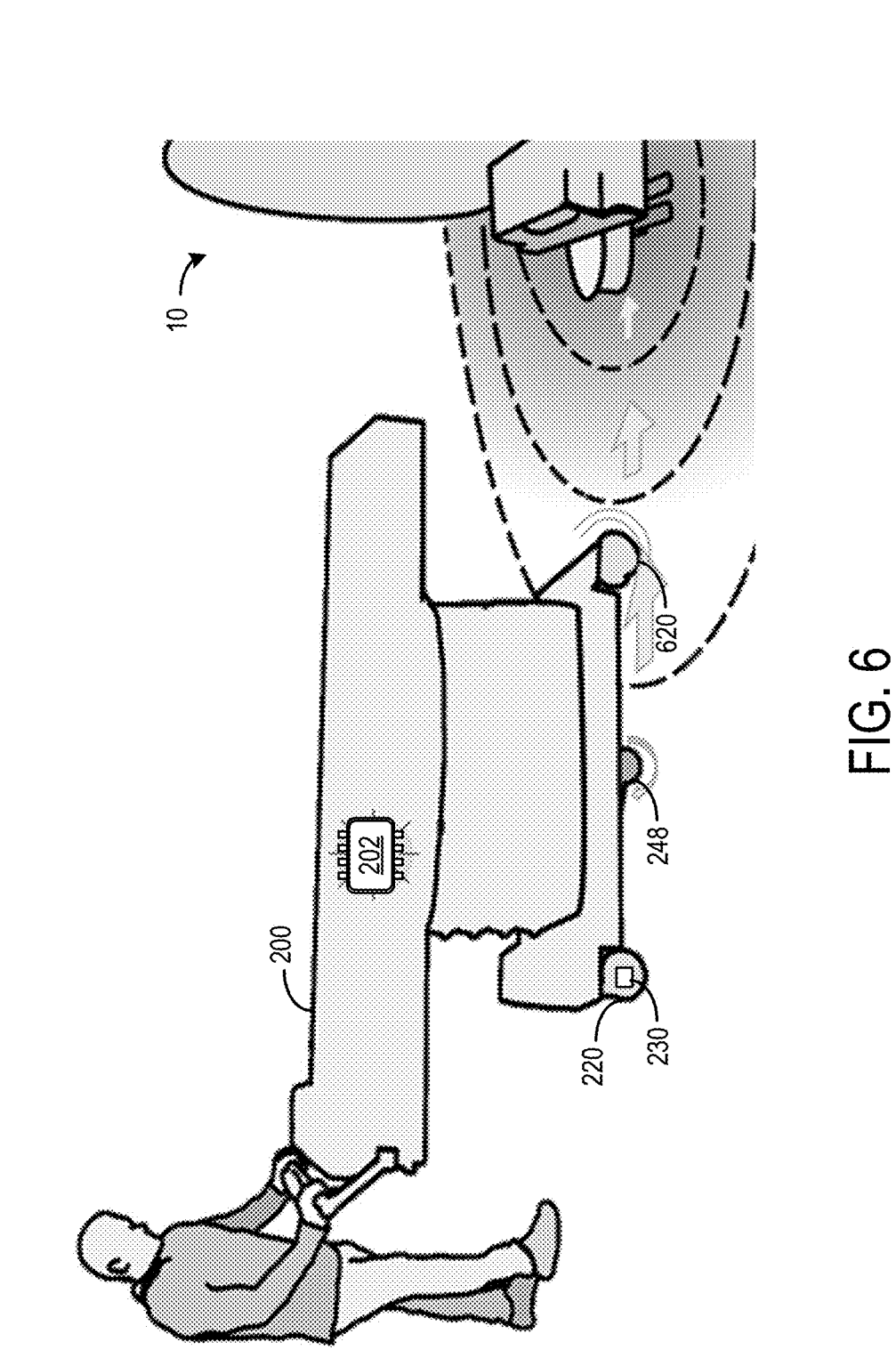
FIG. 6 is an illustration of augmenting transmission of a user input to one or more wheel actuators of the manually driven subject table of FIG. 2 based on the strength or the direction of a magnetic field, as detected by the passive sensor, according to an embodiment of the disclosure.
Figure 8:
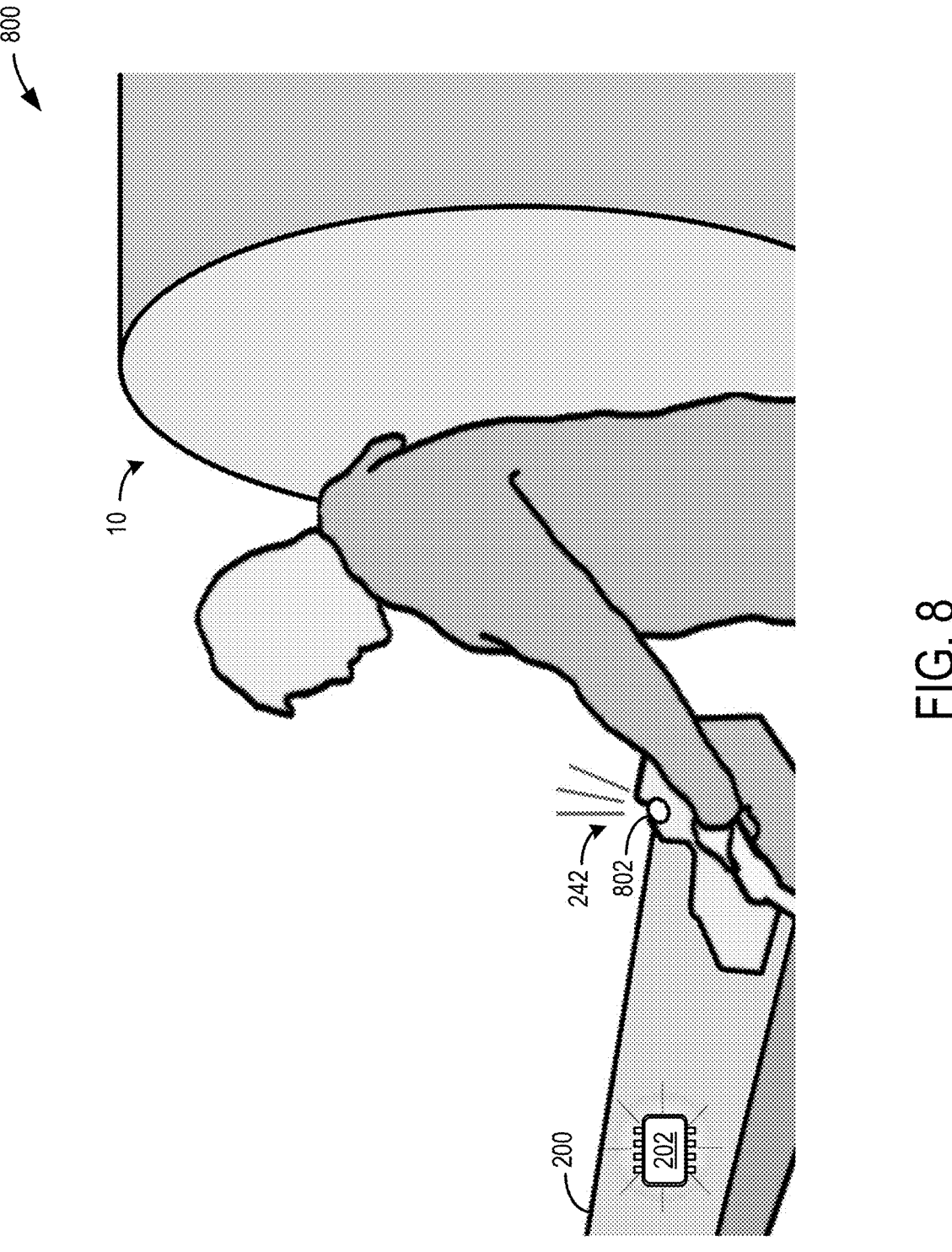
FIG. 8 is an illustration of augmenting transmission of a user input to one or more actuators of a table control panel of the manually driven subject table of FIG. 2 based on the strength or the direction of a magnetic field, as detected by the passive sensor, according to an embodiment of the disclosure.
Figure 9:
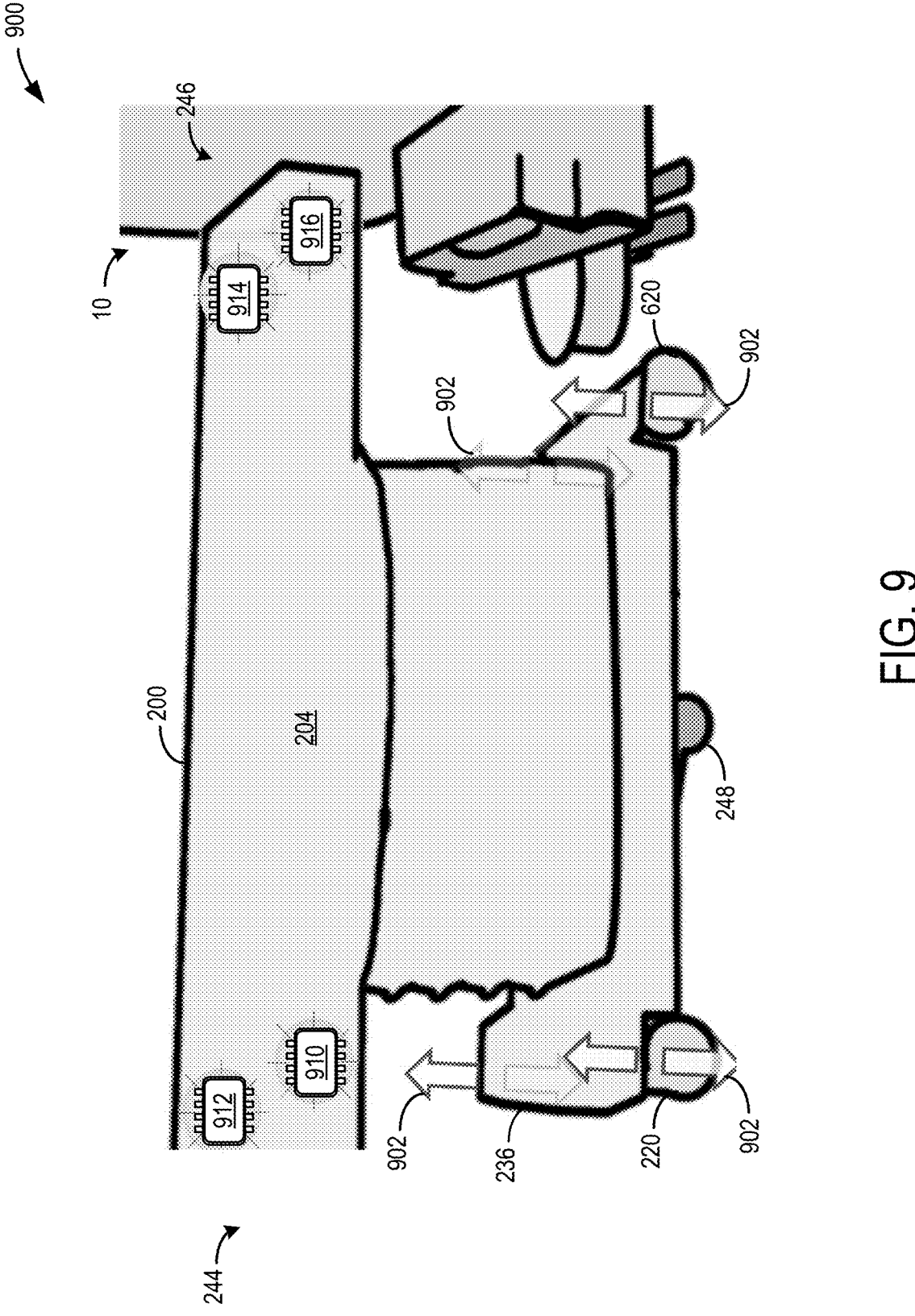
FIG. 9 shows an illustration of augmenting transmission of a user input to one or more actuators of an adjustable height mechanism of the manually driven subject table of FIG. 2 to adjust a planar angle of the manually driven subject table based on the strength or the direction of a magnetic field, as detected by the passive sensor, according to an embodiment of the disclosure.
Figure 10:
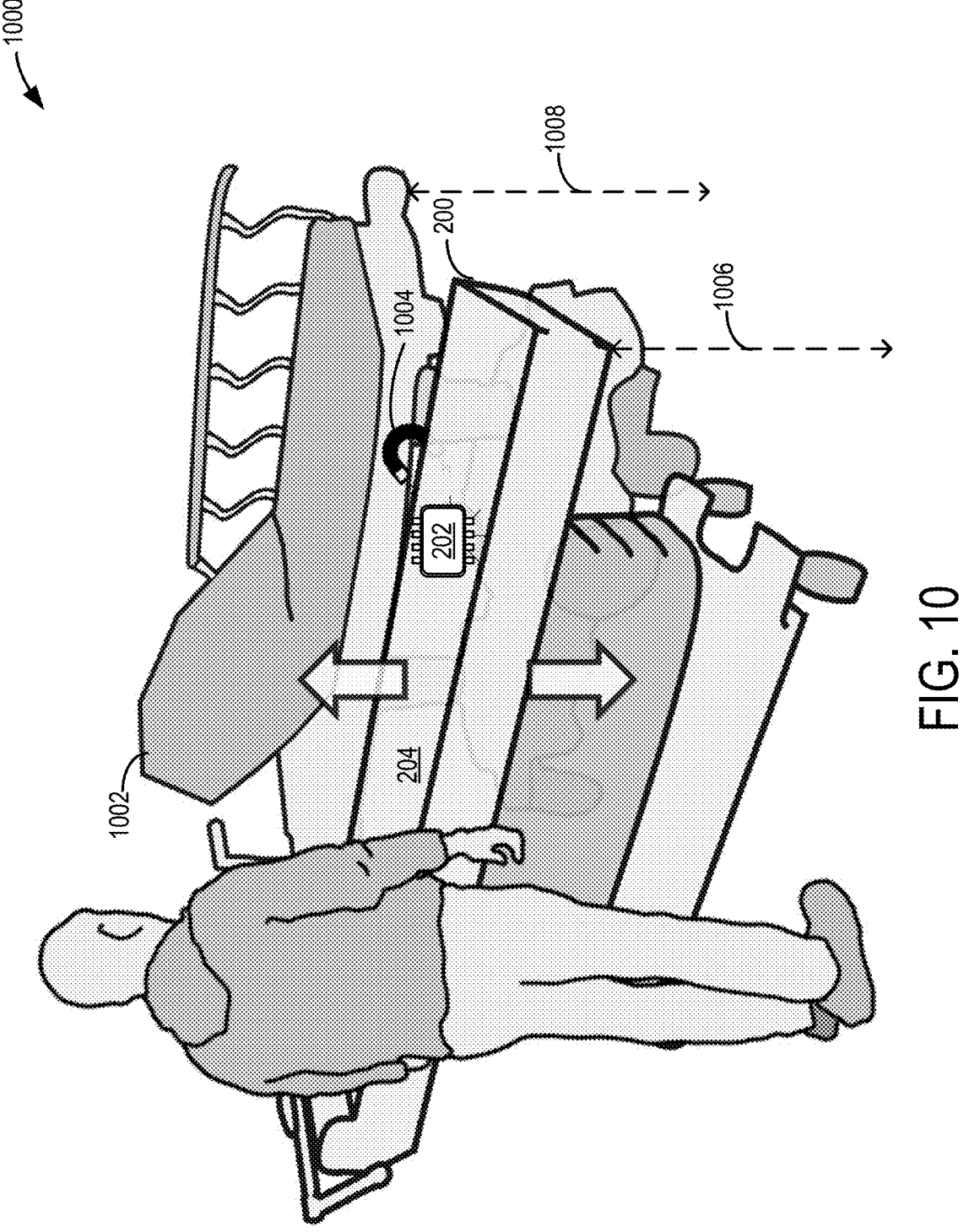
FIG. 10 shows an illustration of augmenting transmission of a user input to one or more actuators of an adjustable height mechanism of the manually driven subject table of FIG. 2 to adjust a height based on a strength or a direction of a magnetic field as detected by the passive sensor, according to an embodiment of the disclosure.

FIG. 1 shows an example medical imaging system in which a manually driven subject table having a passive sensor may be included. FIG. 2 shows an example of a manually driven subject table which includes at least one passive sensor, a user input device, and one or more actuators, each of which are communicably coupled to a controller. FIG. 3 illustrates a method for augmenting transmission of a user input to one or more actuators of the manually driven subject table based on a strength or a direction of a magnetic field as detected by the passive sensor. FIG. 4 illustrates a method for calibrating one or more passive sensors of the subject table of FIG. 2. FIG. 5 illustrates an example field map of a magnetic field used to determine augmentation of user input transmission. Example augmentations to user inputs based on a strength and/or a direction of a magnetic field as detected by the passive sensor are described with respect to FIGS. 6-10. FIG. 6 shows an illustration of augmenting transmission of a user input to one or more wheel actuators based on the strength or the direction of a magnetic field, as detected by the passive sensor. FIG. 7 shows an illustration of augmenting transmission of a user input to one or more docking actuators of the manually driven subject table based on a strength or a direction of a magnetic field as detected by the passive sensor. FIG. 8 shows an illustration of augmenting transmission of a user input to a table control panel (TCP), including a display device, to indicate desired adjustment to a position and/or an orientation of the manually driven subject table based on the strength or the direction of a magnetic field, as detected by the passive sensor. FIG. 9 shows an illustration of augmenting transmission of a user input to the TCP to indicate desired adjustment to a planar angle of the manually driven subject table based on the strength or the direction of a magnetic field, as detected by the passive sensor. FIG. 10 shows an illustration of augmenting transmission of a user input to the TCP to indicate desired adjustment to a height of the manually driven subject table based on a strength or a direction of a magnetic field as detected by the passive sensor.

In some embodiments, the manually driven subject table may be included in a medical system and may operate as a patient table on which a patient is positioned. As the patient table, the manually driven subject table may be used to position a patient with respect to a medical imaging system, such as a magnetic resonance imaging (MRI) system, which generates a magnetic field for imaging the patient. FIG. 1 shows a MRI apparatus 10, which is an example imaging system into which the manually driven subject table may be inserted, docked, or otherwise removably coupled. In the example of FIG. 1, the manually driven subject table is referred to as a patient table 26, as further described herein.

The MRI apparatus 10 that includes a magnetostatic field magnet unit 12, a gradient coil unit 13, an RF coil unit 14, an RF body or volume coil unit 15, a transmit/receive (T/R) switch 20, an RF driver unit 22, a gradient coil driver unit 23, a data acquisition unit 24, a controller unit 25, a patient table 26, a data processing unit 31, an operating console unit 32, and a display unit 33. In some embodiments, the RF coil unit 14 is a surface coil, which is a local coil typically placed proximate to the anatomy of interest of a subject 16. Herein, the RF body coil unit 15 is a transmit coil that transmits RF signals, and the local surface RF coil unit 14 receives the MR signals. As such, the transmit body coil (e.g., RF body coil unit 15) and the surface receive coil (e.g., RF coil unit 14) are separate but electromagnetically coupled components. The MRI apparatus 10 transmits electromagnetic pulse signals to the subject 16 placed in an imaging space 18 with a static magnetic field formed to perform a scan for obtaining magnetic resonance signals from the subject 16. One or more images of the subject 16 can be reconstructed based on the magnetic resonance signals thus obtained by the scan.

The magnetostatic field magnet unit 12 includes, for example, an annular superconducting magnet, which is mounted within a toroidal vacuum vessel. The magnet defines a cylindrical space surrounding the subject 16 and generates a constant magnetostatic field $B_0$.

The MRI apparatus 10 also includes a gradient coil unit 13 that forms a gradient magnetic field in the imaging space 18 so as to provide the magnetic resonance signals received by the RF coil arrays with three-dimensional positional information. The gradient coil unit 13 includes three gradient coil systems, each of which generates a gradient magnetic field along one of three spatial axes perpendicular to each other, and generates a gradient field in each of a frequency encoding direction, a phase encoding direction, and a slice selection direction in accordance with the imaging condition. More specifically, the gradient coil unit 13 applies a gradient field in the slice selection direction (or scan direction) of the subject 16, to select the slice; and the RF body coil unit 15 or the local RF coil arrays may transmit an RF pulse to a selected slice of the subject 16. The gradient coil unit 13 also applies a gradient field in the phase encoding direction of the subject 16 to phase encode the magnetic resonance signals from the slice excited by the RF pulse. The gradient coil unit 13 then applies a gradient field in the frequency encoding direction of the subject 16 to frequency encode the magnetic resonance signals from the slice excited by the RF pulse.

The RF coil unit 14 is disposed, for example, to enclose the region to be imaged of the subject 16. In some embodiments, the RF coil unit 14 may be referred to as the surface coil or the receive coil. In the imaging space 18 where the constant magnetostatic field $B_0$ is formed by the magneto-static field magnet unit 12, the RF coil unit 15 transmits, based on a control signal from the controller unit 25, an RF pulse that is an electromagnet wave to the subject 16 and thereby generates a high-frequency magnetic field $B_1$. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magneti-zation vector. In some embodiments, the RF coil unit 14 may transmit the RF pulse and receive the MR signal. In other embodiments, the RF coil unit 14 may only be used for receiving the MR signals, but not transmitting the RF pulse.

The RF body coil unit 15 is disposed, for example, to enclose the imaging space 18, and produces RF magnetic field pulses orthogonal to the main magnetic field $B_0$ pro-duced by the magnetostatic field magnet unit 12 within the imaging space 18 to excite the nuclei. In contrast to the RF coil unit 14, which may be disconnected from the MRI apparatus 10 and replaced with another RF coil unit, the RF body coil unit 15 is fixedly attached and connected to the MRI apparatus 10. Furthermore, whereas local coils such as the RF coil unit 14 can transmit to or receive signals from only a localized region of the subject 16, the RF body coil unit 15 generally has a larger coverage area. The RF body coil unit 15 may be used to transmit or receive signals to the whole body of the subject 16, for example. Using receive-only local coils and transmit body coils provides a uniform RF excitation and image uniformity at the expense of high RF power deposited in the subject. For a transmit-receive local coil, the local coil provides the RF excitation to the region of interest and receives the MR signal, thereby decreasing the RF power deposited in the subject. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode or a transmit-receive mode. The coils of the local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coils (e.g., RF coil unit 15) and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic reso-nance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the data processing unit 31.

The MRI apparatus 10 includes a table 26 for placing the subject 16 thereon. The subject 16 may be moved inside and outside the imaging space 18 by moving the table 26 based on control signals from the controller unit 25.

The controller unit 25 includes a computer and a record-ing medium on which a program to be executed by the computer is recorded. The program when executed by the computer causes various parts of the apparatus to carry out operations corresponding to pre-determined scanning. The recording medium may comprise, for example, a ROM, flexible disk, hard disk, optical disk, magneto-optical disk, CD-ROM, or non-volatile memory card. The controller unit 25 is connected to the operating console unit 32 and pro-cesses the operation signals input to the operating console unit 32 and furthermore controls the table 26, RF driver unit 22, gradient coil driver unit 23, and data acquisition unit 24 by outputting control signals to them. The controller unit 25 also controls, to obtain a desired image, the data processing unit 31 and the display unit 33 based on operation signals received from the operating console unit 32.

The operating console unit 32 includes user input devices such as a touchscreen, keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform predetermined data processing is recorded. The data processing unit 31 is connected to the controller unit 25 and performs data processing based on control signals received from the controller unit 25. The data processing unit 31 is also connected to the data acquisition unit 24 and generates spectrum data by applying various image processing operations to the magnetic resonance signals output from the data acquisition unit 24.

The display unit 33 includes a display device and displays an image on the display screen of the display device based on control signals received from the controller unit 25. The display unit 33 displays, for example, an image regarding an input item about which the operator inputs operation data from the operating console unit 32. The display unit 33 also displays a two-dimensional (2D) slice image or three-dimensional (3D) image of the subject 16 generated by the data processing unit 31.

Though a MRI system is described by way of example, it should be understood that the present techniques may also be useful when applied to other devices which generate a magnetic field and for which it is desirable to position a manually driven subject table (e.g., the table 26) with respect to the magnetic field strength or direction. The present discussion of an MRI imaging modality is provided merely as an example of one suitable modality having a magnetic field. An additional example of a device which generates a magnetic field is described with respect to FIG. 10.

Turning to FIG. 2, an embodiment of a manually driven subject table 200 having a passive sensor 202 is shown. The manually driven subject table 200, herein also referred to as "the subject table" for brevity, may be an example of the patient table 26 of FIG. 1. The subject table 200 may additionally or alternatively be an example of a table used to transport subjects, such as patients, throughout a medical environment including a magnetic field source (e.g., which generates a magnetic field in which the subject table 200 may be positioned), such as a MRI apparatus. The subject table 200 includes a bed 204, a handle 206, an adjustable height mechanism 208, one or more undriven wheels, and a table control panel (TCP) 242. Further elements of the subject table 200 are described herein. The subject table 200 is communicably coupled, via a wired or a wireless connection, to a controller 210.

The passive sensor 202 may be any sensor which detects and responds to energy available in an environment without itself outputting energy to elicit a response from the environment. The passive sensor 202 described herein is configured to detect at least one of a strength of a magnetic field or a direction of a magnetic field in real-time. For example, the passive sensor 202 may be a Hall sensor. In some embodiments, the passive sensor 202 may be configured to detect both the strength and the direction of the magnetic field in real-time. Further, the passive sensor 202 the strength and/or the direction of the magnetic field in real time, and detect the other parameter (e.g., the strength or the direction) at periodic intervals. The passive sensor 202 is communicably coupled to the controller 210 via a wired or wireless connection. In some embodiments, the passive sensor 202 is integrated in the controller 210 when the controller 210 is positioned in or on the subject table 200, as further described herein. In some embodiments, the passive sensor 202 is positioned in or on the subject table 200 and communicably coupled, via a wired or wireless connection, to the controller 210 positioned on a device other than the subject table 200, such as in a user interface device. In some embodiments, the subject table 200 may include more than one passive sensor 202. For example, as further described with respect to FIG. 9, a passive sensor may be positioned in the subject table 200 at each of four corners of the bed 204, and a strength and a magnitude of a magnetic field at each passive sensor may be compared to determine an angle, and thus a levelness, of the bed 204.

The controller 210 includes a processor 240 configured to execute machine-readable instructions stored in a non-transitory memory 238 of the controller 210. The processor 240 may be single core or multi-core, and the programs executed by the processor 240 may be configured for parallel or distributed processing. In some embodiments, the processor 240 may optionally include individual components that are distributed throughout two or more devices, which may be remotely located and/or configured for coordinated processing. In some embodiments, one or more aspects of the processor 240 may be virtualized and executed by remotely-accessible networked computing devices configured in a cloud computing configuration. In some embodiments, the processor 240 may include other electronic components capable of carrying out processing functions, such as a digital signal processor, a field-programmable gate array (FPGA), or a graphics board. In some embodiments, the processor 240 may include multiple electronic components capable of carrying out processing functions. For example, the processor 240 may include two or more electronic components selected from a plurality of possible electronic components, including a central processor, a digital signal processor, a field-programmable gate array, and a graphics board. In still further embodiments, the processor 240 may be configured as a graphical processing unit (GPU), including parallel computing architecture and parallel processing capabilities. As further described herein, in some embodiments, the controller 210 may be integrated in the subject table 200. In other embodiments, the controller 210 may be part of a medical device, such as the MRI apparatus 10 of FIG. 1 (e.g., the controller 210 may be an example of the controller unit 25).

The subject table 200 is defined herein as "manually driven", meaning that a motion and a direction of movement of the subject table 200 is provided by a user input. For example, the user may be a healthcare provider. The user input may be a pushing force applied by the user to the subject table 200, for example, at the handle 206, to drive the subject table 200 in a first direction indicated by a first arrow 212. The user may also apply a pulling force to the subject table 200, for example, at the handle 206, to drive the subject table 200 in a second direction indicated by a second arrow 214. As further described herein, subject table 200 includes one or more undriven wheels which may rotate as a result of force applied to the subject table 200 (e.g., from a user input) and may not be motor driven or otherwise autonomously driven. In some embodiments, the one or more undriven wheels may be caster-like wheels and be adjustable among a roll state, a steer-lock state, and a brake-lock state. The roll state enables 360-degree rotation of the respective undriven wheel about an axis to enable the subject table 200 to be driven in directions other than the first direction and the second direction. The steer state enables linear motion of the respective undriven wheel (e.g., the first direction and/or the second direction). The brake-lock state halts rotation of the respective undriven wheel, which may halt motion of the subject table 200. The user may also change a direction of the subject table 200 (e.g., may turn the subject table 200), for example, by applying disproportionate push and/or pull forces to a first side 216 and a second side 218 of the handle 206 when the undriven wheels are in the roll state. The direction of the subject table 200 may be changed (e.g., the subject table 200 may be turned) while moving in the first direction or the second direction, or when the subject table 200 is stationary.

In the example of FIG. 2, the undriven wheel of the subject table 200 includes a first electronic caster 220, a second electronic caster 222, a third electronic caster 224, and a fourth electronic caster (not shown, opposite the third electronic caster 224 and the first electronic caster 220). The fourth electronic caster is shown in the orientation of the subject table 200 of FIGS. 6, 7, and 9 (e.g., the fourth electronic caster 620). Each of the first electronic caster 220, the second electronic caster 222, the third electronic caster 224, and the fourth electronic caster 620 (as shown in FIGS.

6, 7, and 9), collectively the one or more electronic casters, may include a brake in each respective caster. Each of the one or more electronic casters may further include a caster actuator which, as further described herein, may enable the respective electronic caster to be adjusted among the roll state, the brake-lock state, and the steer-lock state in response to a user input and augmentation of the user input based on the strength and the direction, respectively, of the magnetic field as detected by the passive sensor 202.

Each of the one or more electronic casters may be coupled to a base 236 of the subject table 200 in a manner which allows a wheel of each of the one or more casters to swivel about a respective axis, as is the nature of a conventional caster. The subject table 200 further includes one or more caster actuators configured to control a mode of one or more electronic caster coupled thereto. For example, the one or more caster actuators includes a first caster actuator 230 coupled to the first electronic caster 220, a second caster actuator 232 coupled to the second electronic caster 222, a third caster actuator 234 coupled to the third electronic caster 224, and a fourth caster actuator (not shown) coupled to the fourth electronic caster. Each of the one or more caster actuators is communicably coupled to the controller 210. As further described herein, the controller 210 may augment transmission of a user input to one or more caster actuators to control state changes of the respective caster(s) based on the strength and the direction, respectively, of the magnetic field as detected by the passive sensor 202. The controller may receive the strength and/or the direction of the magnetic field as detected by the passive sensor in real-time. That is to say, the controller may receive the strength and/or the direction in real-time.

The subject table 200 further includes a drive wheel 248. The drive wheel 248 is shown in FIG. 2 as a dashed line circle, as the drive wheel 248 may not be visualized in the orientation of the subject table 200 shown in FIG. 2. The drive wheel 248 may be visualized in the orientation of the subject table 200 shown in FIGS. 6, 7, and 9. The drive wheel 248 may include a small motor configured to provide supplemental driving force to user input force (e.g., the small motor may not be configured to itself drive the manually driven subject table 200). The small motor may be communicably coupled to the controller 210 and may be controlled by a drive wheel actuator (not shown) to assist or restrict rotation of the drive wheel 248 in response to a user input and augmentation of the user input based on the strength and the direction, respectively, of the magnetic field as detected by the passive sensor 202. For example, augmentation of the user input may include actuating the small motor to provide supplemental torque to the drive wheel 248, which may reduce a demand of user-provided force to move the subject table 200.

The manually driven subject table 200 may further include a manual brake 226. The manual brake 226 may be actuated by a user, for example, by depressing the manual brake 226, to halt motion of the subject table 200. The manual brake 226 may additionally or alternatively be controlled via an input (e.g., a user input) received at a table control panel (TCP) 242, as further described herein. The manual brake 226 may be at a first end 244 of the subject table 200. At a second end 246, opposite the first end 244, the subject table 200 may include a docking system (not shown) which enables docking of the subject table 200 with other devices and/or systems. For example, as described with respect to FIG. 7, the subject table 200 may be docked with a MRI apparatus (e.g., the MRI apparatus 10 of FIG. 1).

The subject table 200 may further include a table control panel (TCP) 242. The TCP may receive user input via one or more of a display screen, a microphone, a keyboard and a mouse, and so on. The TCP may further provide output such as notifications via the display screen, a sound-emitting speaker, or other device for outputting a notification. In the embodiment shown in FIG. 2, the TCP 242 may be positioned on the handle 206 of the subject table 200. In other embodiments, the TCP 242 may be positioned on or integrated in the bed 204 of the subject table 200. In further embodiments, the TCP 242 may be integrated in a device other than the subject table 200. For example, the TCP 242 may be integrated in a user device which is communicably coupled to the controller 210 and to the passive sensor 202 via the controller 210. The controller 210 is communicably connected to the TCP 242 via a wired or wireless connection. The controller 210 may command the TCP 242 to output a notification in response to a strength or a direction of a magnetic field as detected by the passive sensor 202. For example, as further described herein with respect to FIGS. 8-9, the TCP 242 may output a noise, illuminate a light, or otherwise output a notification indicating that the subject table 200 is in an undesirable position or orientation based on the strength or the direction of the magnetic field as detected by the passive sensor 202.

A force sensor 250, such as a load cell, may be integrated in the subject table 200 to detect a mechanical force (e.g., tension, pressure, compression, torque) applied to the subject table 200 (e.g., by a user via a user input). For example, the force sensor 250 may be integrated in the handle 206 or at the first end 244 of the bed 204 of the subject table 200. The force sensor 250 may be communicably coupled to the controller 210 via a wired or a wireless connection. As further described herein, mechanical force detected by the force sensor may be used in addition to the strength and the direction of the magnetic field as detected by the passive sensor 202 to augment transmission of a user input to one or more actuators of the subject table 200.

The adjustable height mechanism 208 of the subject table 200 couples the base 236 to the bed 204, and enables the bed 204 to be adjusted a variable distance 228 from the base 236. The adjustable height mechanism 208 may include, for example, a scissor lift, a telescoping lift, or other compact device for adjusting a variable distance. The adjustable height mechanism 208 may further include a motor (not shown) coupled to the device for assisting adjustment of the variable distance 228, and communicably coupled to the controller 210. As further described herein with respect to FIGS. 6-10, in response to a strength or a direction of the magnetic field as detected by the passive sensor 202, the controller 210 may actuate a notification system (e.g., the TCP 242) to output a notification indicating desired actions (e.g., a user input) to adjust the variable distance 228. In some embodiments, the controller 210 may further command actuation of the motor to provide supplemental assistance to a user input to adjust the variable distance 228 by expanding or contracting the respective device.

Turning to FIG. 3, a method 300 is illustrated for controlling a manually driven subject table (e.g., the manually driven subject table 200 of FIG. 2) based on a strength or a direction of a magnetic field as detected by a passive sensor of the subject table (e.g., the passive sensor 202). The manually driven subject table is positioned in the magnetic field, and the passive sensor may detect the strength or the direction of the magnetic field in real-time. The method 300 may be implemented by one or more of the above described systems, including the controller unit 25 of FIG. 1 and/or the controller 210 of FIG. 2, or other embodiments of the systems described with respect to FIGS. 1-2. As such, the method 300 may be stored as executable instructions in non-transitory memory, such as the non-transitory memory 238 of FIG. 2, and executed by a processor, such as the processor 240 of FIG. 2.

The subject table having the passive sensor integrated therein may, at different times, be positioned at different orientations with respect to, and different distances from, a magnetic field-emitting device (e.g., a magnet). For example, the subject table may be positioned a first distance from a MRI apparatus (e.g., the MRI apparatus 10) with a handle (e.g., the handle 206) of the subject table facing towards the MRI apparatus and a bed (e.g., the bed 204) of the subject table extending away from the MRI apparatus. The subject table may at a different time be positioned a second distance from the MRI apparatus, where the second distance is less than the first distance. The subject table may further be oriented such that the handle faces away from the MRI apparatus and the bed extends towards the MRI apparatus.

At 302, a user input is received by the manually driven subject table and detected by the controller. The user input may be, for example, a force applied to the handle of the manually driven subject table to push, pull, and/or steer the manually driven subject table. The force may be detected by a force sensor (e.g., the force sensor 250), such as a load cell, and output a signal to the controller which is proportional to a mechanical force (e.g., tension, pressure, compression, torque) applied by the user (e.g., the user input). Additionally or alternatively, the user input may be provided via the TCP and/or another user input device communicably coupled to the controller.

At 304, a strength and/or a direction of a magnetic field as detected by a passive sensor is received by the controller. A strength of the magnetic field as detected by the passive sensor may indicate a distance that the subject table is from the magnet. A direction of the magnetic field as detected by the passive sensor may indicate an orientation of the subject table with respect to the magnet. For example, when a direction of the magnetic field as detected by the passive sensor is directed away from the magnet, the subject table may be in a desirable orientation (e.g., in an orientation at which the subject table may be docked to a MRI apparatus, as further described with respect to FIGS. 6-7). Alternatively, when the direction of the magnetic field as detected by the passive sensor is directed towards the magnet, the subject table may be in an undesirable orientation (e.g., a docking element of the subject table may be oriented away from a docking element of an MRI apparatus, as further described with respect to FIGS. 6-7). The direction of the magnetic field as detected by the passive sensor of the subject table may in some embodiments indicate a detailed orientation of the subject table with respect to the magnet. For example, when the magnetic field is directed towards the magnet and at an obtuse angle, the subject table may be positioned at an angle with respect to the magnet and in a desirable orientation (e.g., a docking element of the subject table oriented towards a docking element of the MRI apparatus). As further described herein, when the direction of the magnetic field as detected by the passive sensor is in line (e.g., aligned along a linear axis) with the magnet (e.g., aligned with a centerline extending through the imaging space of the MRI apparatus of FIG. 1), the subject table may be in a desirable position at which the subject table may be docked with a device having the magnet (e.g., the MRI apparatus of FIG. 1, a second subject table, and so on).

Further, when a strength of the magnetic field is relatively high compared to a strength of the magnet (e.g., 0.4 Tesla (T) for a 0.5 T magnet of an MRI apparatus), the subject table may be a relatively small distance from the magnet (e.g., 1 meter (m)). When the strength of the magnetic field is relatively low compared to a strength of the magnet (e.g., 0.05 T for a 0.5 T magnet), the subject table may be a relatively large distance from the magnet (e.g., 5 m). In some embodiments, the passive sensor may be configured to detect both the strength and the direction of the magnetic field in real-time. Further, the passive sensor may detect one of the strength and the direction of the magnetic field in real time, and detect the other parameter (e.g., the strength or the direction of the magnetic field) at periodic intervals. In some embodiments, the passive sensor may detect the strength or the direction of the magnetic field in real-time based on a selected parameter, for example, user input via a user input device (e.g., the operating console unit 32).

At 306, a field map is accessed, wherein the field map represents a spatial distribution of a magnetic field, and a position and/or an orientation of the subject table are identified using the field map and the strength and/or the direction of the magnetic field, respectively, as detected by the passive sensor. The field map may be stored in the non-transitory memory of the controller (e.g., the non-transitory memory 238 of the controller 210 of FIG. 2) and accessed by the processor (e.g., the processor 240) to compare the strength and/or the direction of the magnetic field, as detected by the passive sensor, to the field map. The field map may further include desired behaviors for the subject table in different regions of the magnetic field. Calibration of the passive sensor and desired behaviors using the field map is described with respect to FIG. 4. An example field map is described with respect to FIG. 5.

At 308, transmission of the user input to one or more actuators of the manually driven subject table is augmented, based on the position and the orientation identified at operation 306. Example behaviors are described with respect to FIGS. 6-10. Behaviors may include an ability of one or more electronic casters of the subject table to move linearly, swivel/rotate, and/or remain stationary, an amount of supplemental torque provided to the drive wheel, a mode of a docking system of the subject table, a notification status of a notification system (e.g., the TCP), and actuation of an adjustable height mechanism. For example, a drive wheel actuator (e.g., of a drive wheel) which is communicably coupled to the controller may adjust a maximum drive speed of the manually driven subject table by adding, removing, or augmenting a maximum speed threshold of the manually driven subject table in response to the manually driven subject table being in the first region. In response to the user input having a force which causes a speed of the manually driven subject table to equal or exceed the maximum speed threshold, the controller may actuate a brake of one or more undriven wheels and/or of a drive wheel to reduce the speed of the manually driven subject table. In another example, the controller may adjust a set of one or more undriven wheels and/or a drive wheel to a steer-lock position where each wheel of the set of one or more undriven wheels and/or the drive wheel are parallel to a length of the manually driven subject table in response to the manually driven subject table being in a first orientation with respect to a magnet generating the magnetic field as determined by the position and/or the orientation detected by the passive sensor. The controller may further disable the set of one or more undriven wheels and/or the drive wheel from changing among a steer-lock state, a brake-lock state, or a roll state. The method 300 ends.

In this way, the controller which is communicably coupled to the passive sensor may generate and deliver a control parameter for one or more actuators of the manually driven subject table based on the strength or the direction of the magnetic field as detected by the passive sensor. Behaviors which are input by a user (e.g., a user input, such as applying force to a handle of the manually driven subject table to drive and/or steer) may be augmented by the controller based on the strength and/or the direction of the magnetic field as detected by the passive sensor.

Prior to implementation of a method for adjusting a behavior of a manually driven subject table based on a strength and/or a direction of a magnetic field as detected by a passive sensor of the manually driven subject table (e.g., the method 300), the passive sensor may be calibrated to establish a strength and a direction of the magnetic field at which the subject table is at a desirable distance and in a desirable orientation with respect to the magnet generating the magnetic field. The desirable distance and the desirable orientation of the subject table may be, for example, when the subject table is docked with an MRI apparatus (e.g., the MRI apparatus 10 of FIG. 1), when the subject table is adjacent to and at a level height with a subject transport device (e.g., a patient bed, as further described with respect to FIG. 10), and so on. Calibrating the passive sensor may include, in some embodiments, generating a field map of strengths and directions of the magnetic field in a space (e.g., an imaging room) in which the subject table may be positioned.

FIG. 4 illustrates a method 400 for calibrating a passive sensor of the manually driven subject table (e.g., the subject table 200 of FIG. 2). In some embodiments, the subject table includes more than one passive sensor. In these embodiments, each of one or more passive sensors of the subject table may be calibrated according to the method 400. The method 400 may be implemented by one or more of the above described systems, including the controller unit 25 of FIG. 1 and/or the controller 210 of FIG. 2. As such, the method 400 may be stored as executable instructions in non-transitory memory, such as the non-transitory memory 238 of FIG. 2, and executed by a processor, such as the processor 240 of FIG. 2.

At 402, the manually driven subject table is positioned at the desirable distance and in the desirable orientation with respect to the magnet generating the magnetic field, and each of the at least one passive sensors of the subject table are calibrated. The subject table may be positioned by a user, for example, by applying force to a handle (e.g., the handle 206) of the subject table when the one or more electronic casters of the subject table are in a drive position or a steer position and the manual brake is disengaged. In some embodiments, calibrating each of the at least one passive sensors includes zeroing each of the passive sensors. For example, a strength of the magnetic field as detected by the passive sensor when the subject table is positioned at the desirable distance with respect to the magnet (e.g., docked with the MRI apparatus) may be set as equal to zero. Further, zeroing each of the passive sensors may include setting a direction of the magnetic field as detected by the passive sensor when the subject table is positioned at the desirable orientation with respect to the magnet (e.g., docked with the MRI apparatus) to null (e.g., having no direction). In this way, as the subject table is moved away from the magnet (e.g., a distance between the magnet and the subject table increases), a strength of the magnetic field detected by the passive sensor may decrease.

Some embodiments of the passive sensors may output the detected strength of the magnetic field as a negative number, wherein a larger negative number indicates a greater distance of the subject table from the magnet. Alternatively, some embodiments of the passive sensors may output a strength of the magnetic field as a positive number, wherein a larger positive number indicates a greater distance of the subject table from the magnet. The strength of the magnetic field as output of the passive sensors may or may not be directly proportionate to an actual strength of the magnetic field. For example, the strength of the magnetic field may exponentially decrease as a distance between the subject table and the magnet increases at a linear rate.

A direction of the magnetic field as output by some embodiments of the passive sensor may be opposite a true direction of the magnetic field. For example, as shown in the field map of FIG. 5, the magnetic field may be polar and point away from the magnet at a south pole and point towards the magnet at the north pole. However, in some embodiments of the passive sensor where calibrating the passive sensor includes setting a direction of the magnetic field to null when the subject table is in the desirable orientation and at the desirable distance with respect to the magnet, the direction of the magnetic field as detected by the passive sensor may point towards the magnet, irrespective of which pole the subject table is adjacent to. In other embodiments, the passive sensor may be calibrated to output the true direction of the magnetic field (e.g., showing polarity of the magnet).

At 404, as the manually driven subject table is moved throughout the magnetic field (e.g., moved to different positions in an imaging room), the passive sensor continuously (e.g., in real-time) detects and records a strength and a direction of the magnetic field. The subject table may be moved throughout the magnetic field to a number of predetermined locations (e.g., where a distance between the subject table and the magnet is known), and the strength and the direction of the magnetic field as detected by the calibrated passive sensor are recorded, along with the known distance between the subject table and the magnet.

Desired behaviors of the subject table may be associated with different positions of the subject table with respect to the magnet. For example, when a distance between the subject table and the magnet is greater than or equal to 5 m, it may be desirable for the electronic casters of the subject to be in a drive position and/or a steer position, which may enable the subject table to be manually driven towards the magnet. In another example, when an orientation of the subject table is not desirable (e.g., a docking system of the subject table is not aligned with a dock system of the MRI apparatus), the notification system of the subject table may output a notification indicating the undesirable orientation. Further behavior examples are described with respect to FIGS. 6-10.

At 406, a field map is updated to represent the calibrated passive sensor in the magnetic field and stored for future access. The field map may illustrate a spatial distribution, including a strength and a direction, or a magnetic field, as further described with respect to FIG. 5. For example, a strength of the magnetic field as detected by the passive sensor may be associated with desired behaviors for a given distance. As described with respect to operation 404, desired behaviors may be established (e.g., by a user, by a manufacturer, and so on) for different distance ranges with respect to the magnet. A strength or range of strengths of the magnetic field as detected by the passive sensor may be recorded when the subject table is known to be in the given distance range. Then, the strength or range of strengths may be associated with the desired behaviors of the given distance range. Associations made between behaviors and detected strength and/or direction of the magnetic field according to the method 400 may be stored as a dataset in non-transitory memory of a controller (e.g., non-transitory memory 238 of the controller 210) and be called upon to adjust behaviors of the subject table based on the strength and/or the direction of the magnetic field as detected by the passive sensor of the subject table (e.g., as described with respect to FIG. 3).

FIG. 5 illustrates an example of a field map 500 which illustrates a spatial distribution, including a strength and a direction, or a magnetic field. The field map 500 may be stored on a non-transitory memory (e.g., the non-transitory memory 238) of a controller (e.g., the controller 210) and accessed by a processor of the controller (e.g., the processor 240) to identify a position and an orientation of a subject table (e.g., the subject table 200 of FIG. 2) based on a strength and a direction, respectively, of the magnetic field as detected by a passive sensor of the subject table.

The field map 500 includes a grid 502, a first dashed ring 504, a second dashed ring 506, and a magnet 508. The grid 502 represents a two-dimensional space in which the subject table can move/be moved (e.g., a top-down view of a floor of an imaging room). The first dashed ring 504 and the second dashed ring 506 represent a magnetic field generated and emitted by the magnet 508. The magnet 508 may be, for example a magnet of an MRI apparatus, such as the MRI apparatus 10 of FIG. 1, a magnet attached to a subject transport device, as further described with respect to FIG. 10, or other magnet attached to a device with respect to which the subject table may be positioned. In the example of FIG. 5, the magnet 508 is a 0.5 T magnet, as is illustrated in the grid 502 by the label "0.5 T" at the magnet 508. A strength of the magnetic field at different locations on the grid 502 are labeled. For example, the magnetic field strength is relatively stronger (e.g., greater T) at positions on the grid 502 closer to the magnet 508, and the magnetic field strength is relatively weaker (e.g., lower T) at positions on the grid 502 further from the magnet 508. The magnetic field is strongest (e.g., 0.5 T) at the magnet 508. Arrows on each of the first dashed ring 504 and the second dashed ring 506 indicate a direction of the magnetic field. For example, arrows on the first dashed ring 504 and the second dashed ring 506 on a left side 514 of the magnet 508 point away from the magnet 508, and arrows on the first dashed ring 504 and the second dashed ring 506 on a right side 516 of the magnet 508 point towards the magnet 508, illustrating polarity of the magnet 508 (e.g., a south pole on the left side 514 and a north pole on the right side 516).

As described with respect to FIG. 4, desired behaviors of the subject table may be associated with different positions of the subject table with respect to the magnet. This may be represented in the field map 500 by one or more squares of the grid 502 having defined associated behaviors for the subject table. For example, a first square 520 may be a first distance (e.g., 2.5 m) from the magnet 508. At the first square 520, a strength of the magnetic field may be approximately 0.2 T, and a direction of the magnetic field may be parallel to the magnet 508. Thus, desirable behaviors may include those which enable the subject table to be moved towards the magnet 508. The desirable behaviors may include adjusting one or more electronic casters of the subject table to a steer-lock state, a brake-lock state, or a roll state. When calibrating the one or more passive sensors of the subject table as described with respect to FIG. 4, a strength of the magnetic field as detected by at least one passive sensor may be recorded and associated with the first distance. In some embodiments, the strength of the magnetic field as detected by a passive sensor may or may not be equal to the true strength of the magnetic field (e.g., 0.2 T), however due to the calibration method, the desired behaviors at the first distance may be associated with the detected strength. Further, the detected magnetic field direction may also be recorded in associated with the desired behaviors. In this way, during execution of the method 300, when the passive sensor detects the strength of the magnetic field and the direction of the magnetic field associated with the first square 520, the controller (e.g., the controller 210) may adjust behaviors of the subject table accordingly.

Described herein with respect to FIGS. 6-10 are further examples for adjusting behaviors of a manually driven subject table (e.g., the subject table 200 of FIG. 2) based on a strength and/or a direction of a magnetic field as detected by one or more passive sensors of the subject table. The methods described herein with respect to FIGS. 6-10 may be stored as executable instructions in non-transitory memory, such as the non-transitory memory 238 of FIG. 2, and executed by a processor, such as the processor 240 of FIG. 2.

FIG. 6 shows an illustration 600 of modifying subject table behaviors based on a proximity to the magnet of the MRI apparatus 10 as detected by the passive sensor 202. In some embodiments, the subject table 200 may be in motion when the controller receives the strength and/or the direction of the magnetic field. Based on the received strength and/or magnitude of the magnetic field (e.g., as detected by the passive sensor 202) and information provided by the field map, the controller may determine that the subject table 200 is moving towards the magnet of the MRI apparatus 10 at a first rate. The first rate may be greater than a first threshold rate, where the first threshold rate is a speed between one and three miles per hour (mph). In response to the first rate being greater than the first threshold rate, the controller may generate and output a control signal to actuate a caster actuator of one or more caster actuators to adjust a maximum allowable drive speed of the drive wheel to less than the first threshold rate. For example, the first caster actuator 230 of the first electronic caster 220 may receive the control signal from the controller and reduce a maximum rotational speed of the first electronic caster 220. In some embodiments, the controller may additionally or alternatively generate and output a control parameter for the supplemental motor (not shown) to provide torque in a direction opposite the direction of the subject table motion to reduce the first rate to less than the first threshold rate.

The passive sensor 202 may continuously detect the strength and the direction of the magnetic field as the subject table 200 is in motion, and the controller may continuously update behaviors of the subject table 200 based on the detected strength and direction of the magnetic field. For example, the maximum rotational speed of one or more electronic casters of the subject table 200 may be progressively decreased as a distance between the subject table 200 and the MRI apparatus 10 decreases, thus slowing a drive speed of the subject table 200.

When a strength of the magnetic field as detected by the passive sensor is less than a first strength threshold, the controller may generate and output a control parameter to each of the one or more casters of the subject table to halt electronic caster state changes. For example, this control parameter may prevent each electronic caster of the subject table from changing among the drive position, the steer position, and/or the brake position. The electronic casters may thus remain in whichever of the drive position, the steer position, and/or the brake position they were in prior to the detected strength of the magnetic field being less than the first strength threshold. In this way, docking of the subject table with the MRI apparatus may be simplified, as undesired motion of the subject table may be prevented.

In a further example, adjusting behavior of one or more electronic casters of the subject table 200 based on the strength and/or the direction of the magnetic field as detected by the passive sensor 202 may include adjusting for force sensor inaccuracies as the subject table 200 moves within the magnetic field. The subject table 200 may idle (e.g., not be in motion) undocked from the MRI apparatus. A user may apply force to the subject table 200 (e.g., to the handle) to drive the subject table 200. An interruption in electronic drive (e.g., halting of one or more electronic casters) may occur while the manual brake 226 and the electronic drive (e.g., the electronic casters) are enabled, in which case the controller may sample the passive sensor 202 and a force sensor of the subject table 200 to correct for force sensor inaccuracies. For example, if the controller determines that a velocity of the subject table 200 is greater than a threshold velocity, and a strength of the magnetic field is greater than a threshold magnitude, the controller may perform a force sensor compensation algorithm to determine an amount of force to supplement (e.g., via a supplement motor of the subject table 200, as described with respect to FIG. 2). If the controller determines that the velocity of the subject table 200 is less than the threshold velocity or if the strength of the magnetic field is less than the threshold magnitude, the controller may not adjust an amount of supplemental force.

In a further embodiment, following interruption of the electronic drive, the controller may sample the velocity of the subject table and, in response to the velocity being less than the threshold velocity, disable a steer lock and electronic drive. For example, one or more electronic casters of the subject table may be adjusted to the steer position, and the supplemental motor may be deactivated. In response to the velocity being greater than the threshold velocity, the controller may reduce a maximum velocity of the subject table, as described above. In this way, a maximum electronic drive speed of the subject table may be proportionately reduced as a distance of the subject table to the magnet decreases. As further discussed herein, a height of the subject table may be automatically increased as the subject table approaches the magnet.

Turning to FIG. 7, example images are shown illustrating a method for adjusting system behaviors, including behaviors of the subject table 200 and behaviors of an MRI apparatus (e.g., the MRI apparatus 10 of FIG. 1), based on the strength and/or the direction of the magnetic field as detected by the passive sensor of the subject table. A first image 702 shows the subject table 200 and the MRI apparatus 10 in an undocked configuration. A second image 704 shows the subject table 200 and the MRI apparatus 10 in a docked configuration.

The MRI apparatus 10 includes a dock 710 into which the subject table 200 may be docked (e.g., a docking system 720 of the subject table 200). Based on the received strength of the magnetic field as detected in real-time by the passive sensor 202 of the subject table 200, the controller may determine that the subject table 200 is within a first proximity range of the magnet, and thus the MRI apparatus 10. The first proximity range may be, for example, one to two meters. Further, the controller may determine whether or not the subject table 200 is in a desirable orientation for docking based on the direction of the magnetic field as detected by the passive sensor 202. When the controller determines that the subject table 200 is not in the desirable orientation and/or is not within the first proximity range, the controller may generate and output a control signal to one or more caster actuators of the respective one or more electronic casters to adjust the electronic casters among a drive position and a steer position. This may enable the subject table 200 to be manually maneuvered to the desirable orientation and within the first proximity range.

In response to determination that the subject table 200 is in the first proximity range and having the desired orientation, the controller may generate and output a control signal to each of a docking actuator of the docking system 720 of the subject table 200 and a dock actuator of the dock 710 of the MRI apparatus 10 to prepare for dock engagement. For example, the dock 710 of the MRI apparatus 10 may open to receive the docking system 720 of the subject table 200, and the docking system 720 may extend from the subject table 200. In this way, behaviors of one or more devices may be adjusted based on the position and orientation of the subject table 200 as determined based on the strength and direction, respectively, of the magnetic field as detected by the passive sensor 202 of the subject table 200.

FIG. 8 shows an illustration 800 of operation of a notification system of a subject table (e.g., the subject table 200 of FIG. 2) based on a strength and/or a direction of a magnetic field as detected by a passive sensor of the subject table. The notification system may be the TCP 242 of FIG. 2. In the example of FIG. 8, the TCP 242 includes a light which may illuminate to indicate the subject table is in an undesirable position and/or orientation. As described with respect to FIG. 2, in other embodiments, the TCP 242 may include additional or alternative notification devices, such as a speaker for audio output and/or a screen for visual output.

As described above with respect to the method 300, the controller may receive a strength and/or a direction of a magnetic field in real-time and access a field map to determine that the manually driven subject table 200 is in a first orientation with respect to a magnet generating the magnetic field (e.g., a magnet of the MRI apparatus 10). Based on the field map, the first orientation may not enable docking of the manually driven subject table with the MRI apparatus 10. The controller may generate and output a notification control parameter for the TCP 242, where the notification control parameter commands the notification system to generate and output a notification indicating that the manually driven subject table 200 is in an undesirable orientation for docking with the MRI apparatus 10. For example, a light 802 of the TCP 242 may be illuminated (e.g., solid light, flashing light, and so on). In response to determination that the subject table 200 is in the first orientation, the controller may further generate and output a caster control parameter for one or more caster actuators of the electronic casters. The caster control parameter may command the caster actuator to adjust a respective electronic caster to a roll state.

In this way, a notification (e.g., herein, a visual indicator) may be output by the subject table, based on the position and/or orientation of the subject table as determined using the strength and/or direction, respectively, of a magnetic field detected by a passive sensor of the subject table. The notification may indicate to a user that the subject table is in an undesirable position and/or orientation. In some embodiments, the notification may further indicate that behaviors of the subject table have been adjusted by the controller to enable movement of the subject table to a desirable position and/or orientation.

FIG. 9 shows an illustration 900 of adjusting a level of a bed of a subject table (e.g., the subject table 200 of FIG. 2) based on a strength and/or a direction of a magnetic field as detected by two or more passive sensors of the subject table. As described with respect to FIG. 2, the subject table 200 may include more than one passive sensor. In the example of FIG. 9, the subject table 200 includes four passive sensors: a first passive sensor 910 in a first corner of the first end 244, a second passive sensor 912 in a second corner of the first end 244, a third passive sensor 914 in a third corner of the second end 246, and a fourth passive sensor 916 in a fourth corner of the second end 246. For example, the four passive sensors may be integrated in the bed 204 of the subject table 200. In some embodiments, the subject table 200 may further include a caster height adjuster in each of the first electronic caster 220, the second electronic caster, the third electronic caster, and the fourth electronic caster 620, where the caster height actuator is communicably coupled to the controller and may adjust a height of a respective electronic caster independent of the other electronic casters.

The controller may receive a strength and/or a direction of a magnetic field from each of the first passive sensor 910, the second passive sensor 912, the third passive sensor 914, and the fourth passive sensor 916 in real-time. The controller may compare the strength and direction of the magnetic field as detected by each passive sensor to determine an orientation and levelness of the bed 204 of the subject table 200. The controller may generate and output a control parameter for one or more of the passive sensors (e.g., the same or different control parameters) to adjust lateral and skew of the bed 204 based on the passive sensor outputs. For example, a control parameter may be sent to one or more caster actuators of the subject table 200 to actuate a caster height actuator to adjust an elevated height of the base 236 of the subject table 200 at each of the electronic casters, as indicated by arrows 902. This may assist in installation of the subject table 200 with respect to the MRI apparatus 10, for example, to assist in adjusting the bed 204 of the subject table 200 to be level. Further, in some embodiments, the controller may output data regarding a levelness of the bed 204 to a display device (e.g., a user input device having a display) to indicate potential adjustments which may be made to level the bed 204.

As briefly described herein, the manually driven subject table having one or more passive sensors configured to detect a magnitude and a direction of the magnetic field in real-time may be used with systems which have a magnetic field other than a MRI apparatus. FIG. 10 shows an illustration 1000 of a subject table (e.g., the subject table 200) used in collaboration with a patient transport device 1002. The patient transport device 1002 may be, for example, a hospital bed, gurney, stretcher, or other device for transporting a patient. The patient transport device 1002 may include a magnetic field generating device 1004 which generates a magnetic field. In other embodiments, a removable magnetic field generating device may be provided as the magnetic field generating device 1004, and may be removably attached to the patient transport device 1002. The magnetic field generating device 1004 could be a permanent magnet, or an electrical powered device that generates a magnetic field. The passive sensor 202 of the subject table 200 may detect a strength and a direction of the magnetic field generated by the magnet 1004 in the same way that the passive sensor 202 detects the strength and the direction of the magnetic field generated by the magnet of the MRI apparatus as described herein.

As described above with respect to the method 300, the controller may receive a strength and/or a direction of the magnetic field in real-time and access a field map to determine a position of the manually driven subject table 200 with respect to the patient transport device 1002. Specifically, the passive sensor 202 may determine a height 1006 of the subject table 200 with respect to the patient transport device 1002. For example, it may be desirable for the height 1006 of the subject table 200 to be equal to or slightly greater (e.g., 1 to 5 inches) than a height 1008 of the patient transport device 1002. A strength of the magnetic field as detected by the passive sensor 202 may indicate the height 1006 of the subject table 200 with respect to the patient transport device 1002. The controller may generate and output a control parameter which may command a motor or other actuator of the adjustable height mechanism 208 of the subject table 200 to increase or decrease the height 1006 of the subject table 200. This may assist in automatically positioning the subject table 200 at a desirable height for patient transfer between the subject table 200 and the patient transport device 1002.

The technical effect of adjusting behaviors of a manually driven subject table based on a strength and/or a direction of a magnetic field as detected by a passive sensor of the subject table is increased sensor reliability, redundancy, and workflow simplification. A position, an orientation, and a height of the subject table may be automatically adjusted by a controller of the subject table based on the strength and the direction of the magnetic field, thus assisting user-driven positioning of the subject table, which may increase an accuracy of subject table positioning and decrease a time spent positioning and potentially repositioning the subject table.

The disclosure also provides support for a medical imaging system, comprising: a manually driven subject table having a passive sensor configured to detect in real-time a strength or a direction of a magnetic field, and a controller communicably coupled to the passive sensor and configured with instructions stored on non-transitory memory that, when executed, cause the controller to augment transmission of a user input to one or more actuators of the manually driven subject table based on the strength or the direction of the magnetic field as detected by the passive sensor. In a first example of the system, the magnetic field is generated by a magnet of a magnetic resonance imaging (MRI) system. In a second example of the system, optionally including the first example, the magnetic field is generated by a magnet attached to a subject transport device. In a third example of the system, optionally including one or both of the first and second examples, the manually driven subject table comprises one or more undriven wheels for positioning the manually driven subject table. In a fourth example of the system, optionally including one or more or each of the first through third examples, the system further comprises: an electronic caster-style wheel of the one or more undriven wheels, the electronic caster-style wheel having a caster actuator communicably coupled to the controller and configured to adjust the electronic caster-style wheel among a steer-lock state, a brake-lock state, or a roll state based on the strength or the direction of the magnetic field as detected by the passive sensor. In a fifth example of the system, optionally including one or more or each of the first through fourth examples, the system further comprises: a drive wheel having a drive wheel actuator, the drive wheel actuator communicably coupled to the controller and configured to adjust a maximum drive speed of the manually driven subject table based on the strength or the direction of the magnetic field as detected by the passive sensor. In a sixth example of the system, optionally including one or more or each of the first through fifth examples, the manually driven subject table further comprises a force sensor integrated in a handle positioned at a first end of the manually driven subject table, the force sensor communicably coupled to the controller. In a seventh example of the system, optionally including one or more or each of the first through sixth examples, the manually driven subject table comprises an adjustable height mechanism which includes a height actuator controlled by the controller to adjust a height of the manually driven subject table based on the strength and/or the direction of the magnetic field as detected by the passive sensor. In an eighth example of the system, optionally including one or more or each of the first through seventh examples, the system further comprises: a notification system controlled by the controller to output a notification via the notification system based on the strength and/or the direction of the magnetic field as detected by the passive sensor. In a ninth example of the system, optionally including one or more or each of the first through eighth examples, the manually driven subject table includes a docking system having at least one docking actuator controlled by the controller to prepare the manually driven subject table for engagement or disengagement with a dock of a magnetic field-generating device, based on the strength and/or the direction of the magnetic field as detected by the passive sensor. In a tenth example of the system, optionally including one or more or each of the first through ninth examples, the controller is integrated in the manually driven subject table.

The disclosure also provides support for a method for controlling a manually driven subject table, comprising: receiving a user input to the manually driven subject table, receiving a strength and a direction of a magnetic field detected in real-time using a passive sensor implemented in a manually driven subject table, accessing a field map representing a spatial distribution of the magnetic field and identifying a position and an orientation of the manually driven subject table based on the strength and the direction, respectively, of the magnetic field, and augmenting transmission of the user input to one or more actuators of the manually driven subject table based on the position and the orientation of the manually driven subject table. In a first example of the method, receiving the user input comprises receiving, via a force sensor of the manually driven subject table, a force applied to a handle of the manually driven subject table to push, pull, and/or steer the manually driven subject table. In a second example of the method, optionally including the first example, accessing the field map further comprises accessing desired augmentation of the user input to the manually driven subject table for the identified position and orientation of the manually driven subject table. In a third example of the method, optionally including one or both of the first and second examples, augmenting transmission of the user input comprises: determining whether the position of the manually driven subject table is within a first region of the magnetic field, adding, removing, or augmenting a maximum speed threshold of the manually driven subject table in response to the manually driven subject table being in the first region, and in response to the user input having a force which causes a speed of the manually driven subject table to equal or exceed the maximum speed threshold, actuating a brake of one or more undriven wheels and/or of a drive wheel to reduce the speed of the manually driven subject table. In a fourth example of the method, optionally including one or more or each of the first through third examples, the method further comprises: calibrating the passive sensor of the manually driven subject table by: docking the manually driven subject table to a magnet generating the magnetic field and zeroing the passive sensor of the manually driven subject table, undocking the manually driven subject table from the magnet, moving the manually driven subject table throughout the magnetic field, and detecting the strength and the direction of the magnetic field using the passive sensor, and updating the strength and the direction of the magnetic field at positions on the field map to represent the spatial distribution of the magnetic field. In a fifth example of the method, optionally including one or more or each of the first through fourth examples, augmenting transmission of the user input comprises: determining whether the position of the manually driven subject table is in a first orientation with respect to a magnet generating the magnetic field, the first orientation enabling docking of the manually driven subject table with the magnet, in response to the manually driven subject table being in the first orientation, adjusting a set of one or more undriven wheels and/or a drive wheel to a steer-lock position where each wheel of the set of one or more undriven wheels and/or the drive wheel are parallel to a length of the manually driven subject table, and disabling the set of one or more undriven wheels and/or the drive wheel from changing among a steer-lock state, a brake-lock state, or a roll state.

The disclosure also provides support for a medical imaging system, comprising: a magnet configured to selectively generate a magnetic field, a manually driven subject table having at least one passive sensor configured to detect in real-time a strength and/or a direction of the magnetic field, one or more undriven wheels, a drive wheel, a docking system, a table control panel (TCP), and a controller communicably coupled to the passive sensor and configured with instructions stored on non-transitory memory that, when executed, cause the controller to: compare the strength and/or the direction of the magnetic field identified by the passive sensor to a field map representing a spatial distribution of the magnetic field to identify a position and an orientation, respectively, of the manually driven subject table with respect to the magnet, determine a desired behavior of the manually driven subject table based on the position and the orientation of the manually driven subject table, and add, remove, and/or augment operating parameters of the manually driven subject table to augment transmission of a user input received by the controller to one or more actuators of the manually driven subject table based on the strength or the direction of the magnetic field as detected by the passive sensor. In a first example of the system, the manually driven subject table includes at least one passive sensor on each of a first end and a second end, opposite the first end, of the manually driven subject table, and the controller is further configured with instructions stored on non-transitory memory that, when executed, cause the controller to compare the strength and the direction of the magnetic field identified by each passive sensor to each other to determine a levelness of the manually driven subject table, and generate and output a notification to the TCP indicating the levelness of the manually driven subject table. In a second example of the system, optionally including the first example, the magnet is positioned on a side of a subject transport table, and the controller is further configured with instructions stored on non-transitory memory that, when executed, cause the controller to employ a gradient descent algorithm using the strength and the direction of the magnetic field identified by the at least one passive sensor to determine a desired height of the subject transport table and output a notification via the TCP indicating desired adjustment of the manually driven subject table.

As used herein, an element or step recited in the singular and preceded with the word "a" or "an" should be understood as not excluding plural of said elements or steps, unless such exclusion is explicitly stated. Furthermore, references to "one embodiment" of the present disclosure are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

As used herein, the terms "system" and "module" may include a hardware and/or software system that operates to perform one or more functions. For example, a module or system may include or may be included in a computer processor, controller, or other logic-based device that performs operations based on instructions stored on a tangible and non-transitory computer readable storage medium, such as a computer memory. Alternatively, a module or system may include a hard-wired device that performs operations based on hard-wired logic of the device. Various modules or systems shown in the attached figures may represent the hardware that operates based on software or hardwired instructions, the software that directs hardware to perform the operations, or a combination thereof.

"Systems" or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

This written description uses examples to disclose the disclosure, including the best mode, and also to enable a person of ordinary skill in the relevant art to practice the disclosure, including making and using any devices or systems and performing any incorporated methods. The patentable scope of the disclosure is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical imaging system, comprising:
   a magnet configured to selectively generate a magnetic field, wherein the magnet is positioned on a side of a subject transport table;
   a manually driven subject table having a passive sensor configured to detect in real-time a strength or a direction of the magnetic field, one or more undriven wheels, a drive wheel, a docking system, and a table control panel (TCP); and
   a controller communicably coupled to the passive sensor and configured with instructions stored on non-transitory memory that, when executed, cause the controller to augment transmission of a user input to one or more actuators of the manually driven subject table based on the strength or the direction of the magnetic field as detected by the passive sensor, employ a gradient descent algorithm using the strength and the direction of the magnetic field identified by the at least one passive sensor to determine a desired height of the subject transport table and output a notification via the TCP indicating desired adjustment of the subject table.

2. The medical imaging system of claim 1, wherein the magnetic field is generated by a magnet of a magnetic resonance imaging (MRI) system.

3. The medical imaging system of claim 1, wherein the magnetic field is generated by a magnet attached to a subject transport device.

4. The medical imaging system of claim 1, wherein the manually driven subject table comprises one or more undriven wheels for positioning the manually driven subject table.

5. The medical imaging system of claim 4, further comprising an electronic caster-style wheel of the one or more undriven wheels, the electronic caster-style wheel having a caster actuator communicably coupled to the controller and configured to adjust the electronic caster-style wheel among a steer-lock state, a brake-lock state, or a roll state based on the strength or the direction of the magnetic field as detected by the passive sensor.

6. The medical imaging system of claim 1, further comprising a drive wheel having a drive wheel actuator, the drive wheel actuator communicably coupled to the controller and configured to adjust a maximum drive speed of the manually driven subject table based on the strength or the direction of the magnetic field as detected by the passive sensor.

7. The medical imaging system of claim 1, wherein the manually driven subject table further comprises a force sensor integrated in a handle positioned at a first end of the manually driven subject table, the force sensor communicably coupled to the controller.

8. The medical imaging system of claim 1, wherein the manually driven subject table comprises an adjustable height mechanism which includes a height actuator controlled by the controller to adjust a height of the manually driven subject table based on the strength and/or the direction of the magnetic field as detected by the passive sensor.

9. The medical imaging system of claim 1, further comprising a notification system controlled by the controller to output a notification via the notification system based on the strength and/or the direction of the magnetic field as detected by the passive sensor.

10. The medical imaging system of claim 1, wherein the manually driven subject table includes a docking system having at least one docking actuator controlled by the controller to prepare the manually driven subject table for engagement or disengagement with a dock of a magnetic field-generating device, based on the strength and/or the direction of the magnetic field as detected by the passive sensor.

11. The medical imaging system of claim 1, wherein the controller is integrated in the manually driven subject table.

12. A method for controlling a manually driven subject table, comprising:

receiving a user input to the manually driven subject table;

receiving a strength and a direction of a magnetic field detected in real-time using a passive sensor implemented in a manually driven subject table;

calibrating the passive sensor of the manually driven subject table by:

docking the manually driven subject table to a magnet generating the magnetic field and zeroing the passive sensor of the manually driven subject table;

undocking the manually driven subject table from the magnet, moving the manually driven subject table throughout the magnetic field, and detecting the strength and the direction of the magnetic field using the passive sensor; and updating the strength and the direction of the magnetic field at positions on the field map to represent the spatial distribution of the magnetic field, accessing a field map representing a spatial distribution of the magnetic field and identifying a position and an orientation of the manually driven subject table based on the strength and the direction, respectively, of the magnetic field; and augmenting transmission of the user input to one or more actuators of the manually driven subject table based on the position and the orientation of the manually driven subject table.

13. The method of claim 12, wherein receiving the user input comprises receiving, via a force sensor of the manually driven subject table, a force applied to a handle of the manually driven subject table to push, pull, and/or steer the manually driven subject table.

14. The method of claim 12, wherein accessing the field map further comprises accessing desired augmentation of the user input to the manually driven subject table for the identified position and orientation of the manually driven subject table.

15. The method of claim 12, wherein augmenting transmission of the user input comprises:

determining whether the position of the manually driven subject table is within a first region of the magnetic field;

adding, removing, or augmenting a maximum speed threshold of the manually driven subject table in response to the manually driven subject table being in the first region; and in response to the user input having a force which causes a speed of the manually driven subject table to equal or exceed the maximum speed threshold, actuating a brake of one or more undriven wheels and/or of a drive wheel to reduce the speed of the manually driven subject table.

16. The method of claim 12, wherein augmenting transmission of the user input comprises:

determining whether the position of the manually driven subject table is in a first orientation with respect to a magnet generating the magnetic field, the first orientation enabling docking of the manually driven subject table with the magnet;

in response to the manually driven subject table being in the first orientation, adjusting a set of one or more undriven wheels and/or a drive wheel to a steer-lock position where each wheel of the set of one or more undriven wheels and/or the drive wheel are parallel to a length of the manually driven subject table; and disabling the set of one or more undriven wheels and/or the drive wheel from changing among a steer-lock state, a brake-lock state, or a roll state.

17. A medical imaging system, comprising:

a magnet configured to selectively generate a magnetic field, wherein the magnet is positioned on a side of a subject transport table;

a manually driven subject table having at least one passive sensor configured to detect in real-time a strength and/or a direction of the magnetic field, one or more undriven wheels, a drive wheel, a docking system, and a table control panel (TCP); and a controller communicably coupled to the passive sensor and configured with instructions stored on non-transitory memory that, when executed, cause the controller to:

compare the strength and/or the direction of the magnetic field identified by the passive sensor to a field map representing a spatial distribution of the magnetic field to identify a position and an orientation, respectively, of the manually driven subject table with respect to the magnet;

determine a desired behavior of the manually driven subject table based on the position and the orientation of the manually driven subject table;

employ a gradient descent algorithm using the strength and the direction of the magnetic field identified by the at least one passive sensor to determine a desired height of the subject transport table and output a notification via the TCP indicating desired adjustment of the manually driven subject table; and add, remove, and/or augment operating parameters of the manually driven subject table to augment transmission of a user input received by the controller to one or more actuators of the manually driven subject table based on the strength or the direction of the magnetic field as detected by the passive sensor.

18. The medical imaging system of claim 17, wherein the manually driven subject table includes at least one passive sensor on each of a first end and a second end, opposite the first end, of the manually driven subject table, and the controller is further configured with instructions stored on non-transitory memory that, when executed, cause the controller to compare the strength and the direction of the magnetic field identified by each passive sensor to each other to determine a levelness of the manually driven subject table, and generate and output a notification to the TCP indicating the levelness of the manually driven subject table.

* * * * *